United States Patent
Zappala

(10) Patent No.: US 6,329,398 B1
(45) Date of Patent: Dec. 11, 2001

(54) PREEMPTIVE ANALGESIC AGENT AND METHODS OF USE

(76) Inventor: Stephen M. Zappala, 98 Rattlesnake Hill Rd., Andover, MA (US) 01810

( * ) Notice: Subject to any disclaimer, the term of this patent is extended or adjusted under 35 U.S.C. 154(b) by 0 days.

(21) Appl. No.: 09/821,922

(22) Filed: Mar. 30, 2001

(51) Int. Cl.$^7$ .................................................. A61K 31/445
(52) U.S. Cl. ............................................................ 514/330
(58) Field of Search ..................................... 514/330, 626

(56) References Cited

U.S. PATENT DOCUMENTS

| | | | |
|---|---|---|---|
| 4,562,060 | * 12/1985 | Broberg et al. | 424/28 |
| 5,502,058 | * 3/1996 | Mayer et al. | 514/289 |
| 5,849,334 | * 12/1998 | Rivlin | 424/552 |
| 5,993,836 | * 11/1999 | Castillo | 424/401 |
| 6,075,059 | * 6/2000 | Reader | 514/738 |

* cited by examiner

*Primary Examiner*—James H Reamer
(74) *Attorney, Agent, or Firm*—Mirick, O'Connell, DeMallie & Lougee,

(57) ABSTRACT

A pharmacological agent for use as preemptive analgesia, comprising, 1% lidocaine HCL and 0.25% bupivacaine HCL in a ratio sufficient to provide analgesic effect quickly and for an extended period of time, preferably equal to or less than 10:1.

16 Claims, No Drawings

PREEMPTIVE ANALGESIC AGENT AND METHODS OF USE

FIELD OF THE INVENTION

This invention relates to analgesia and more specifically to preemptive analgesia used as an adjunct to reduce perioperative pain and methods of using the analgesia.

BACKGROUND OF THE INVENTION

It is known that perioperative pain may be reduced by beginning pain reduction therapy before surgery. This early intervention therapy is commonly known as preemptive analgesia, the purpose of which is to reduce the hypersensitization of nociceptors by blocking pain impulses from ever reaching the brain. Essentially, preemptive analgesia prevents the activation of the nociceptors before activation can occur.

Preemptive analgesia has received widespread acceptance as an adjunct to reduce perioperative pain in patients who undergo surgical procedures as generally disclosed by Mayer et al. in U.S. Pat. No. 5,502,058. The technique is well accepted and involves the pharmacological interruption of afferent neurons to the dorsal horns of the spinal cord prior to the delivery of painful stimuli, such as a surgical incision. The anesthetic concept can be applied to most surgical procedures, minimizing postoperative pain as well as the necessity for narcotic or parenteral analgesia. Moreover, patients treated with preemptive analgesia have experienced reduced hospitalizations and a much shorter convalescence.

A clinical shortcoming of preemptive analgesia, however, has been the relatively short duration of the local anesthetic, lidocaine hydrochloride (HCl), which is considered standard and customary. Lidocaine has a very short half-life (less than 30 minutes) and has no inherent contribution to pain control once its local anesthetic effect has resolved. However, lidocaine HCL's extremely rapid onset of action (less than one minute) characterizes it as an attractive agent for neural blockade.

SUMMARY OF THE INVENTION

It is therefore a primary object of this invention to provide an preemptive analgesic agent, and methods of use, that will maintain the clinical benefits of a fast acting analgesic, and yet provide the additional benefits of longer acting regional anesthetics.

It is a further object of the invention to provide an analgesic agent, and methods of use, that will provide a complete neural blockade throughout the surgical procedure and will contribute to the local anesthetic effect for an extended period after the infiltration.

A preferred formulation of the pharmacological agent of the invention for use as preemptive analgesia, comprises: a solution comprising 1% lidocaine HCL and 0.25% bupivacaine HCL in a ratio of less than or equal to 10:1. Other optimal ratios are less than or equal to 5:1; less than or equal to 2:1 and less than or equal to 1:1. The solution preferably further comprises: one or more buffers selected from a group consisting of sodium hydroxide and hydrochloric acid; and a vasoconstrictor such as epinephrine bitartrate in a ratio of about 1:200,000.

The agent is preferably an injectable therapy adapted for one or more applications selected from a group consisting of subcutaneous, caudal, epidural, intramuscular, intradural, intraspinous and peripheral nerve blockade; and/or preferably is capable of providing analgesic effect for at least six hours.

A more specific preferred formulation of the agent of the invention is an injectable preemptive analgesic agent, comprising, 1% lidocaine HCL and 0.25% bupivicaine in an effective ratio capable of providing at least six hours of analgesic therapy, one or more pH buffers, and one or more vasoconstrictors.

The preferred method of the invention for reducing perioperative pain, generally comprises the steps of: providing a sterile, isotonic pharmacologic agent comprising lidocaine and bupivicaine in a ratio less than or equal to 10:1; and introducing said agent as an adjunct for preemptive analgesia before a surgical procedure is initiated. The agent is best introduced as one or more injectable therapies selected from a group consisting of subcutaneous, caudal, epidural, intramuscular, intradural, intraspinous or peripheral nerve blockade. The agent may comprise 1% lidocaine HCL and 0.25% bupivacaine HCL in a ratio sufficient to provide at least six hours of analgesic effect, and may further comprise a vasoconstrictor such as epinephrine bitartrate and/or one or more buffering compounds such as sodium hydroxide and/or hydrochloric acid.

A more specific variation of the method of the invention for reducing perioperative pain, comprises the steps of, providing a sterile, isotonic pharmacologic agent comprising 1% lidocaine, 0.25% bupivicaine and one or more pH buffers; and infiltrating said agent as an adjunct for preemptive analgesia before a surgical procedure is initiated, whereby said agent provides at least six hours of analgesic effect after infiltration.

DETAILED DESCRIPTION OF THE PREFERRED EMBODIMENTS AND METHODS

The preemptive analgesic agent of the invention is adapted to maintain the clinical benefits of the fast acting lidocaine, and yet provide the additional benefits of the longer acting regional anesthetic bupivacaine. The dual drug combination provides a complete neural blockade throughout surgery and contributes to the local anesthetic effect for a period of about six hours after the infiltration.

Lidocaine is a rapidly acting local anesthetic with a short duration (minutes), whereas bupivacaine has a delayed onset of action but a prolonged duration (hours). These two agents act together as an ideal therapy for preemptive analgesia by interrupting local afferents through short and long term neural blockade. The inventive agent generally features a sterile, isotonic solution that combines two pharmacologic therapies, which are routinely employed as local anesthetics, namely, lidocaine, and bupivacaine.

The preferred formulation of the pharmacological agent of the invention comprises dilutions of lidocaine 1% (pKa 7.86) with bupivacaine 0.25% (pKa 8.1) in ratios of less than or equal to 10:1. Other specifically identified optimal ratios are: less than or equal to 5:1; less than or equal to 2:1 and less than or equal to 1:1. The solution has a pH of 7.4. One or more buffers may be used such as sodium hydroxide and/or hydrochloric acid. The agent may further include epinephrine bitartrate 1:200,000, a potent vasoconstrictor that decreases systemic absorption and further prolongs the local anesthetic effect.

The agent is preferably an injectable therapy adapted for one or more applications including subcutaneous, caudal, epidural, intramuscular, intradural, intraspinous and peripheral nerve blockade. The agent should be capable of providing analgesic effect for at least six hours. However, the desired time period may vary depending on the procedural circumstances.

The method of the invention for reducing perioperative pain, generally comprises the steps of: providing the sterile, isotonic pharmacologic agent of the invention described above; and introducing the agent as an adjunct for preemptive analgesia before a surgical procedure is initiated. As noted, the agent is best introduced as one or more injectable therapies selected from a group consisting of subcutaneous, caudal, epidural, intramuscular, intradural, intraspinous or peripheral nerve blockade. The agent used in the method preferably comprises 1% lidocaine HCL and 0.25% bupivacaine HCL in ratios sufficient to provide at least six hours of analgesic effect, and may further comprise epinephrine and/or one or more buffering compounds such as sodium hydroxide and/or hydrochloric acid.

Although specific features of the invention are discussed with some of the formulations and methods and not others, this is for convenience only as some feature may be combined with any or all of the other features in accordance with the invention. Modifications of the formulations and methods will occur to those skilled in the art and are within the following claims.

What is claimed is:

1. A pharmacological agent for use as preemptive analgesia, comprising, a solution comprising 1% lidocaine HCL and 0.25% bupivacaine HCL in a ratio less than or equal to 10:1.

2. The agent of claim 1, wherein said ratio is less than or equal to 5:1.

3. The agent of claim 1, wherein said ratio is less than or equal to 2:1.

4. The agent of claim 1, wherein said ratio is less than or equal to 1:1.

5. The agent of claim 1, wherein said solution further comprises one or more buffers selected from a group consisting of sodium hydroxide and hydrochloric acid.

6. The agent of claim 1, wherein said solution is an injectable therapy for one or more applications selected from a group consisting of subcutaneous, caudal, epidural, intramuscular, intradural, intraspinous and peripheral nerve blockade.

7. The agent of claim 1, wherein said solution further comprises epinephrine bitartrate 1:200,000.

8. The agent of claim 1, wherein said solution is capable of providing analgesic effect for at least six hours.

9. A method of reducing perioperative pain, comprising the steps of,
   providing a sterile, isotonic pharmacologic agent comprising licocaine and bupivicaine in a ratio less than or equal to 10:1; and
   introducing said agent as an adjunct for preemptive analgesia before a surgical procedure is initiated.

10. The method of claim 9, wherein said agent is introduced as one or more injectable therapies selected from a group consisting of subcutaneous, caudal, epidural, intramuscular, intradural, intraspinous or peripheral nerve blockade.

11. The method of claim 9, wherein said agent comprises 1% lidocaine HCL and 0.25% bupivacaine HCL in a ratio sufficient to provide at least six hours of analgesic effect.

12. The method of claim 10, wherein said agent further comprises one or more vasoconstrictors.

13. The method of claim 10, wherein said agent further comprises one or more buffering compounds.

14. The method of claim 13, wherein one or more of said buffering compounds comprises sodium hydroxide.

15. A method of reducing perioperative pain, comprising the steps of,
   providing a sterile, isotonic pharmacologic agent comprising 1% lidocaine, 0.25% bupivicaine and one or more pH buffers; and
   infiltrating said agent as an adjunct for preemptive analgesia before a surgical procedure is initiated, whereby said agent provides at least six hours of analgesic effect after infiltration.

16. An injectable preemptive analgesic agent, comprising, 1% lidocaine HCL and 0.25% bupivicaine in an effective ratio capable of providing at least six hours of analgesic therapy, one or more pH buffers, and one or more vasoconstrictors.

\* \* \* \* \*

UNITED STATES PATENT AND TRADEMARK OFFICE
CERTIFICATE OF CORRECTION

PATENT NO.    : 6,329,398 B1
DATED         : December 11, 2001
INVENTOR(S)   : Stephen M. Zappala It is certified that error appears in the above-identified patent and that said Letters Patent is hereby corrected as shown below:

Title page,
After Item "[22] Filed: Mar. 30, 2001" insert the following paragraph:
-- Related U.S. Application Data
[63] Continuation-in-part of Ser. No. 656,050, September 6, 2000, which is a continuation of Ser. No. 60/152,718, September 7, 1999. --.

Column 1,
Line 2, insert the following paragraph:
-- CROSS-REFERENCE
This is a continuation-in-part of U.S. Patent Application Serial No. 09/656,050, filed on September 6, 2000, which is a continuation of U.S. Provisional Patent Application Serial No. 60/152,718, filed on September 7, 1999, now abandoned. --.

Signed and Sealed this

Tenth Day of August, 2004

JON W. DUDAS
*Acting Director of the United States Patent and Trademark Office*